United States Patent [19]

Cesa et al.

[11] Patent Number: 5,250,721
[45] Date of Patent: Oct. 5, 1993

[54] METHOD FOR STABILIZATION OF CRUDE ACETONITRILE AS OXIDATION OR AMMOXIDATION FEED

[75] Inventors: Mark C. Cesa, South Euclid; Mark R. Bruce, Seven Hills, both of Ohio

[73] Assignee: The Standard Oil Company, Cleveland, Ohio

[21] Appl. No.: 805,216

[22] Filed: Dec. 11, 1991

[51] Int. Cl.$^5$ .................. C07C 253/32; C07C 253/34
[52] U.S. Cl. .................................................... 558/435
[58] Field of Search ........................................ 558/435

[56] References Cited

U.S. PATENT DOCUMENTS

| | | | |
|---|---|---|---|
| 2,351,157 | 6/1944 | Semon | 558/435 X |
| 3,516,789 | 6/1970 | Sennewald et al. | 23/151 |
| 3,911,089 | 10/1975 | Shiraishi et al. | 423/376 |
| 4,287,134 | 9/1981 | Smiley | 558/435 |
| 4,328,075 | 5/1982 | Fitzgibbons et al. | 558/435 X |
| 4,457,905 | 7/1984 | Ebner | 423/376 |
| 4,461,752 | 7/1984 | Sasaki et al. | 423/376 |
| 4,485,079 | 11/1984 | Brazdil et al. | 423/376 |
| 4,521,395 | 6/1985 | Kuechler et al. | 423/376 |
| 4,981,670 | 1/1991 | Dio et al. | 423/376 |

OTHER PUBLICATIONS

Nagastto et al., C. A., vol. 80, 108016a (1974).

*Primary Examiner*—Joseph Paul Brust
*Attorney, Agent, or Firm*—M. F. Esposito; D. J. Untener

[57] ABSTRACT

A method of producing stabilized crude acetonitrile (i.e. acetonitrile which has been treated to substantially eliminate polymerization of the acetonitrile upon vaporization) which comprises mixing crude acetonitrile, a strong base and aldehyde together, heating to the reflux temperature of the mixture to stabilize the crude acetonitrile and recovering the stabilize acetonitrile. This stabilized acetonitrile is utilized to manufacture hydrogen cyanide.

6 Claims, No Drawings

METHOD FOR STABILIZATION OF CRUDE ACETONITRILE AS OXIDATION OR AMMOXIDATION FEED

BACKGROUND OF THE INVENTION

The present invention is directed to the stabilization of crude acetonitrile, in particular, crude acetonitrile produced as a coproduct during the manufacture of acrylonitrile. In another aspect of the present invention, the stabilized crude acetonitrile obtained by the process described below is upgraded by catalytic treatment in a fluid bed reactor to produce hydrogen cyanide.

The manufacture of acrylonitrile by the direct reaction of propylene, ammonia and air over a catalyst in a fluid bed reactor is recognized worldwide and referred to as the "Sohio Acrylonitrile Process". In addition to the manufacture of acrylonitrile, the Sohio Acrylonitrile Process produces coproducts such as acetonitrile and hydrogen cyanide. Acetonitrile is a known commercial solvent. Hydrogen cyanide is an important substance which is frequently employed as a starting material for various organic reactions. Any improvements in the yields of these coproducts or upgrading of these coproducts would enhance the economic value of the Sohio Acrylonitrile Process.

Various patents disclose processes for the manufacture of hydrogen cyanide by reacting acetonitrile over ammoxidation or oxidation catalyst. For example, U.S. Pat. No. 3,516,789 discloses a process for the manufacture of hydrogen cyanide by reacting acetonitrile over an ammoxidation catalyst. This patent discloses that the feed of acetonitrile is purified to remove all impurities such as acrylonitrile and hydrogen cyanide. Japan Patent Kokai 73 81816 (CA80:108016a) discloses purification of acetonitrile by adding alkali, heating, treating with formaldehyde and distilling to remove HCN, acrylonitrile, etc. U.S. Pat. No. 3,911,089 discloses the preparation of hydrogen cyanide by the addition of methanol to the ammoxidation reactor used during the production of acrylonitrile. The addition of the methanol increases the yield of hydrogen cyanide. German Patent 1,146,861 discloses hydrogen cyanide production by the reaction of acetonitrile with molecular oxygen over an ammoxidation catalyst. Belgium Patent 623,100 also discloses the reaction of acetonitrile over an ammoxidation catalyst to produce hydrogen cyanide.

It has been observed that the direct vaporization of crude acetonitrile results in substantial plugging or fouling of the apparatus making the commercial practice of the process quite difficult. In U.S. Pat. No. 4,981,670 assigned to the assignees of the present application, crude acetonitrile is used as a source for the direct formation of hydrogen cyanide. A polymerization inhibiting agent is added to eliminate plugging and fouling observed previously during the use of crude acetonitrile for oxidation to HCN. It would be desirable to be able to utilize crude acetonitrile, especially crude acetonitrile coproduct from the Sohio Acrylonitrile Process, as a source for the manufacture of hydrogen cyanide by oxidation or ammoxidation without resorting to the complete purification of the acetonitrile as disclosed in U.S. Pat. No. 3,516,789 or the addition of a polymerization inhibiting agent as set forth in U.S. Pat. No. 4,981,670. The present invention is directed to providing a modified crude acetonitrile source ("stabilized crude acetonitrile") as the source for the manufacture of hydrogen cyanide.

SUMMARY OF THE INVENTION

It is the primary object of the present invention to provide an economical process for the stabilization of crude acetonitrile for use as an oxidation or ammoxidation feed in the preparation of hydrogen cyanide.

It is another object of the present invention to provide a novel procedure for the stabilization of crude acetonitrile. It is still another object of the present invention to provide a process for the stabilization of crude acetonitrile obtained as a coproduct during the manufacture of acrylonitrile.

Additional objects and advantages will be recognized by those having ordinary skill in the art upon reading the specification and the specific embodiments described herein.

To achieve the foregoing objects and advantages of the present invention, the process of the present invention comprises mixing crude acetonitrile with a strong base and aldehyde to form a mixture, heating the mixture to its reflux temperature for a time sufficient to enable the crude acetonitrile to stabilize, and distilling the mixture to recover the stabilized crude acetonitrile.

In a further aspect of the present invention, the process for manufacturing hydrogen cyanide comprises vaporizing stabilized crude acetonitrile, passing the vaporized crude acetonitrile into a reactor where the acetonitrile is mixed with an oxygen containing gas and contacted with a catalyst to produce hydrogen cyanide, and recovering the hydrogen cyanide so produced.

In a preferred embodiment of this aspect of the present invention, the process further comprises introducing ammonia into the reactor.

In still another preferred embodiment of this aspect of the present invention, the oxygen containing gas is air.

In a still further preferred embodiment of this aspect of the present invention, the catalyst is selected from the group consisting of oxidation and/or ammoxidation catalysts, preferably bismuth-iron-molybdenum base oxidation/ammoxidation catalysts.

DETAILED DESCRIPTION OF THE PRESENT INVENTION

The term "crude acetonitrile" as used herein means liquid acetonitrile containing hydrogen cyanide, other impurities and water. The crude acetonitrile used in the present invention can be obtained from any conventional source. However, in the preferred embodiments of the present invention, the crude acetonitrile is a coproduct produced during the manufacture of acrylonitrile. Crude acetonitrile comprises acetonitrile/water azeotrophe containing various organic impurities. For example, crude acetonitrile produced as a coproduct from the Sohio Acrylonitrile Process in addition to containing acetonitrile contains water, hydrogen cyanide, acrylonitrile, acetaldehyde, acetone, methanol, acrolein and oxazole, etc. The relative proportions of the components of the crude acetonitrile can vary over a wide range depending on various conditions. The concentration level of the organic impurities in the crude acetonitrile is usually less than 15 weight percent with no single component found in greater than 2–4 weight percent concentration. Usually crude acetonitrile obtained from the acrylonitrile plant contains between 25 and 85 percent acetonitrile.

The term "stabilized crude acetonitrile" means for purposes of this invention, crude acetonitrile which has been treated according to the process of the present invention, to remove some of the impurities found in crude acetonitrile in order to prevent the polymerization which occurs during vaporization of crude acetonitrile. It is important to note that "stabilized crude acetonitrile" contains impurities at concentrations which are well above those associated with "purified acetonitrile".

The process for the production of stabilized crude acetonitrile according to the present invention comprises mixing crude acetonitrile with a strong base and aldehyde to form a mixture, heating the mixture to its reflux temperature for a time sufficient to enable said crude acetonitrile to stabilize and distilling said mixture to recover the stabilized crude acetonitrile.

The strong base used in this invention can be any strong base stable to crude acetonitrile and soluble in it. Particularly, suitable strong bases are hydroxides of alkali and alkaline earth metals; most preferred are sodium hydroxide and potassium hydroxide. The strong base can be added in pure form, as a mixture of strong bases, or an aqueous solution. In a preferred embodiment of the practice of the present invention, an aqueous solution of sodium or potassium hydroxide of 1–50 weight percent can be used. Typically, the strong base is added to maintain the pH of the crude acetonitrile at between 10 and 14, preferably 11–14, especially preferred being 12–13.8.

The aldehyde used in this invention can be formaldehyde, paraformaldehyde, or $C_2$–$C_6$ saturated aliphatic aldehydes. The preferred aldehyde is formaldehyde. Formaldehyde can be used in pure form or as an aqueous solution. Commercial aqueous formaldehyde solutions of approximately 37 weight percent formaldehyde and about 10–15 weight percent methanol added as a stabilizer are appropriate for the process of the present invention. Usually, the aldehyde is added so that the mole ratio of aldehyde to strong base is between 0.25 and 5.0, with a mole ratio of 0.5 to 2.0 preferred and 0.75 to 1.5 particularly preferred. The temperature of the crude acetonitrile-strong base-aldehyde mixture should be maintained at least 50° C. preferably between 50° to 140° C.

In a further aspect of the present invention, the stabilized crude acetonitrile obtained by the process described above is upgraded by converting it to the more valuable product, hydrogen cyanide. The process for the manufacture of hydrogen cyanide according to the present invention comprises vaporizing the stabilized crude acetonitrile, introducing the vaporized acetonitrile into a reactor wherein the acetonitrile is mixed with a gas containing oxygen and contacted with a catalyst to produce hydrogen cyanide, and recovering the hydrogen cyanide.

In a preferred embodiment of this aspect of the present invention, the stabilized crude acetonitrile vaporization is preferably accomplished by heating the crude acetonitrile in a vaporization/superheater unit. When the crude acetonitrile is fed to the vaporization/superheater unit, the strong base and formaldehyde or other aldehyde are added along with the crude acetonitrile to prevent or substantially minimize the fouling and plugging problems which occur during vaporization and handling of the vaporized crude acetonitrile. After the crude acetonitrile, strong base and aldehyde are fed to the vaporization/superheater unit, the mixture is heated to a temperature sufficient to vaporize acetonitrile (approximately 110° to 130° C.) at an elevated pressure, followed by superheating to about 135° to 140° C. in the superheater unit. Any conventional vaporization/superheater unit may be utilized in the practice of the present invention. Such units can be operated either continuously or in a batch mode.

In a further preferred embodiment of this aspect of the present invention a slip stream of unvaporized material (10 to 35 percent by weight of the feed stream going into the vaporizing unit) is taken out of the vaporization/superheater unit to help further reduce potential fouling of the system and allowing for maintenance of constant vaporized crude acetonitrile composition.

The vaporization/superheater unit is operated at an elevated temperature between 110° to 140° C. It also is operated at an elevated pressure of between 12 to 25 psig. Preferably, the temperature range for vaporization is between 125° to 130° C. and superheating of the crude acetonitrile vapors takes place at between 135° to 140° C. The pressure range for superheating is between 15 to 35 psig, preferably between 20 to 30 psig.

The stabilized crude acetonitrile is fed to a reactor in which it is mixed with a gas containing oxygen (preferably air) and optionally ammonia and brought into contact with an oxidation or ammoxidation catalyst to produce hydrogen cyanide. The hydrogen cyanide is subsequently recovered from the reactor by conventional means (e.g. condensation). The reactor may be any fixed bed or fluid bed reactor useful for catalytic oxidation and ammoxidation reactions. Oxygen may be supplied to the reaction zone either in pure form, as air, or mixtures with inert gases such as nitrogen, helium, argon and the like. Ammonia may be supplied to the reaction zone either as a pure vapor or as a mixture with water (ammonium hydroxide solution) or other inert solvent.

Typically, the vaporized stabilized crude acetonitrile entering the reactor is mixed with the oxygen containing gas and optionally ammonia in the reactor before contacting the catalyst. Either fixed bed or fluid bed reactors and catalysts may be utilized in the practice of the invention. Preferably, a fluid bed reactor and fluid bed catalyst are utilized. Any fluid bed catalyst suitable for conversion to acetonitrile to HCN via oxidation or ammoxidation may be utilized in this aspect of the present invention. Typically, BiFeMoOx promoted catalysts or FeSbOx promoted catalysts are preferred. For specific reference to catalysts suitable in the present invention, see U.S. Pat. Nos. 3,642,930; 3,911,089; 4,228,098 and 3,516,789 herein incorporated by reference.

Reaction temperatures for the preferred vapor phase fluid bed reactions are within the range of 300° to 550° C., preferably 325° to 500° C., especially preferred being 375° to 470° C. Pressures are within the range of 0.1 to 10 atmospheres absolute. The contact time with the mixture of stabilized crude acetonitrile, oxygen containing gas with the catalyst is between 0.5 seconds to 50 seconds, preferably about 0.1 seconds to 20 seconds. The molar ratios of the reaction components can vary within wide limits. For example, 0 to 10 moles ammonia and 0.01 to 40 moles oxygen may be used per mole of acetonitrile in the crude acetonitrile feed. Preferred mole ratio ranges of ammonia and oxygen are 0 to 3.0 per mole of acetonitrile and 0.5 to 10 per mole of acetonitrile, respectively.

In a preferred embodiment of this aspect of the present invention, the stabilized crude acetonitrile is converted to hydrogen cyanide in a separate reactor system and the reactor effluent is fed directly to the propylene ammoxidation quench reactor and the effluent then fed to the propylene ammoxidation absorber column found in the acrylonitrile manufacturing plant. In this manner, the propylene ammoxidation recovery and purification system utilized during the manufacture of acrylonitrile can be used to recover and purify the incremental hydrogen cyanide produced by the oxidation or ammoxidation of the stabilized crude acetonitrile. Any unreacted acetonitrile can be recycled to the stabilization process via the propylene ammoxidation recovery and purification process. However, it is in the scope of this aspect of the present invention that the synthesis of incremental hydrogen cyanide from stabilized crude acetonitrile can be performed during propylene ammoxidation to manufacture acrylonitrile. This is performed by introduction of the stabilized crude acetonitrile produced in accordance with the present invention as a cofeed through the ammoxidation reactor with propylene during the manufacture of acrylonitrile.

The following examples are set forth below only for purposes of illustration.

EXAMPLE 1

1000 mL of crude acetonitrile were placed in a 2 L 3-neck flask affixed with thermometer, magnetic stir bar, reflux condenser, dropping funnel atop the reflux condenser, and distillation apparatus composed of a 30 cm vacuum jacketed fractionating column packed with glass helices and a coldfinger distillation head. The crude acetonitrile was heated with stirring to 72° C., and 24 mL of 50 weight percent aqueous NaOH solution was added dropwise over 10 minutes via the dropping funnel. The reflux condenser and dropping funnel were removed, and the reaction mixture was stirred at reflux (through the fractionating column) for 2 hours. Then the reflux condenser and dropping funnel were re-attached, and 48 mL of 37 weight percent aqueous formaldehyde solution containing 10–15 weight percent methanol were added dropwise over 5 minutes. The reflux condenser and dropping funnel were again removed, and the mixture was stirred at reflux for 45 minutes and then fractionally distilled. 705 mL of distillate of boiling range 73°–85° C., stabilized crude acetonitrile, were collected. Analysis of the distillate showed 74.3 weight percent $CH_3CN$, 18.3 weight percent $H_2O$, less than 15 ppm HCN, and 0.01 weight percent acrylonitrile, and the remainder other organics.

The stabilized crude acetonitrile was mixed with a quantity of liquid ammonia such that the molar ratio of ammonia:acetonitrile was 0.25:1. The stabilized crude acetonitrile:ammonia solution was then pumped through a 1/16" type 316 stainless steel tube, 5.5 feet of which were immersed in a sand bath heated to 410° C., at a flow rate of 3 mL/hr and a pressure of 20–25 psig. The residence time of the liquid feed in the heated zone of the tube was approximately 30 minutes. The effluent from the heated tube was collected in a pressurized vessel. After 302 mL of stabilized crude acetonitrile:ammonia solution were passed through the heated tube over a 69 hour period, no plugging or fouling of the tube was observed, and the tubing showed no change in weight after the experiment.

COMPARATIVE EXAMPLE 1

Untreated crude acetonitrile having the same composition as Example 1 was mixed with a quantity of saturated aqueous ammonium hydroxide solution such that the molar ratio of ammonia:acetonitrile was 0.25:1. The untreated crude acetonitrile:ammonia solution was then pumped through a 1/16" type 316 stainless steel tube, 5.5 feet of which were immersed in a fluidized sand bath heated to 410° C., at a flow rate of 3 mL/hr and a pressure of 20–25 psig. The residence time of the liquid feed in the heated zone of the tube was approximately 30 minutes. After approximately 2 hours, the tubing became plugged at a region of the tubing before the part immersed in the sand bath. The temperature at the site of plugging was approximately 100°–125° C.

COMPARATIVE EXAMPLE 2

209.78 g of crude acetonitrile was placed in a 500 mL 3-neck flask affixed with thermometer, stir bar, septum, and reflux condenser. 4.01 g of solid NaOH were then added at room temperature with stirring. The temperature of the mixture rose rapidly to 30° C., then fell to 28° C. over 1 hour. The mixture was then heated to reflux for 4 hours, then allowed to cool overnight. The mixture was then distilled at atmospheric pressure through a 10 cm vigreaux column to collect 176.3 g of treated crude acetonitrile. Analysis of the treated crude acetonitrile distillate showed 47.4 weight percent $CH_3CN$, 47.3 weight percent $H_2O$, 900 ppm HCN, and 0.02 weight percent acrylonitrile, and the remainder other organics.

The treated crude acetonitrile was mixed with a quantity of liquid ammonia such that the molar ratio of ammonia:acetonitrile was 0.25:1. The treated crude acetonitrile:ammonia solution was then pumped through a 1.16" type 316 stainless steel tube, 5.5 feet of which were immersed in a sand bath heated to 410° C., at a flow rate of 2.5 mL/hr. and a pressure of 20–25 psig. The effluent from the heated tube was collected in a pressurized vessel. After 5.0 mL of stabilized crude acetonitrile:ammonia solution were passed through the heated tube over a 2.2 hour period, plugging of the tube was observed, causing flow of the treated crude acetonitrile:ammonia solution to stop.

EXAMPLE 2

205.4 g of crude acetonitrile was placed in a 500 mL 3-neck flask affixed with thermometer, stir bar, septum, and reflux condenser. 1.18 g of paraformaldehyde and 4.03 g of solid NaOH were then added at room temperature with stirring. The temperature of the mixture rose rapidly to 34° C., then fell to 28° C. over 1 hour. The mixture was then heated to reflux for 4 hours, then allowed to cool overnight. The mixture was then distilled at atmospheric pressure through a 10 cm vigreaux column to collect 175.6 g of stabilized crude acetonitrile of boiling range 71.5° C.–96° C. Analysis of the stabilized crude acetonitrile distillate showed 49.4 weight percent $CH_3CN$, 44.7 weight percent $H_2O$, 54 ppm HCN, and 0.01 weight percent acrylonitrile, and the remainder other organics.

The stabilized crude acetonitrile was mixed with a quantity of liquid ammonia such that the molar ratio of ammonia:acetonitrile was 0.25:1. The stabilized crude acetonitrile:ammonia solution was then pumped through a 1/16" type 316 stainless steel tube, 5.5 feet of which were immersed in a sand bath heated to 410° C., at a flow rate of 2.5 mL/hr. and a pressure of 20-25 psig. The effluent from the heated tube was collected in a pressurized vessel. After 29.1 mL of stabilized crude acetonitrile:ammonia solution were passed through the heated tube over a 8.2 hour period, no plugging or fouling of the tube was observed, and the tubing showed no change in weight after the experiment.

EXAMPLE 3

A continuous reactor for treatment of crude acetonitrile was assembled from a 100 mL volume 316 stainless steel stirred autoclave affixed with inlets for crude acetonitrile solution, aqueous sodium hydroxide solution, and aqueous formaldehyde solution; a drain for bottoms removal; and a tube and receiver for removal of distillate. The feed inlets extended to nearly the bottom of the reactor, and the distillate tube was attached to the head of the reactor. 42 mL of crude acetonitrile having the same composition as Example 1 was placed in the reactor, and the reactor was heated to 72° C. 2.35 g of 25 weight percent aqueous NaOH solution and 2.11 g of 37 weight percent aqueous formaldehyde solution were added, and the mixture was stirred in the autoclave at 72°-80° C. for 1 hour. The reactor was then heated further until distillate began to collect in the receiver. Then feed pumps for crude acetonitrile, aqueous NaOH solution, aqueous formaldehyde solution, and bottoms removal were turned on, and the continuous distillation of treated crude solution was carried out for 60 minutes. During that time 78.0 mL of crude acetonitrile, 5.75 g of 25 weight percent aqueous NaOH solution, and 3.86 g of 37 weight percent aqueous formaldehyde solution were added, 86 mL of stabilized crude acetonitrile distillate were collected as a clear colorless liquid, and 16 mL of bottoms were recovered. Analysis of the stabilized crude acetonitrile distillate showed 56.8 weight percent acetonitrile, 35.7 weight percent $H_2O$, 0.08 weight percent acrylonitrile, 11 ppm HCN, and the remainder other organics.

The stabilized crude acetonitrile was mixed with a quantity of liquid ammonia such that the molar ratio of ammonia:acetonitrile was 0.25:1. The stabilized crude acetonitrile:ammonia solution was then pumped through a 1/16" type 316 stainless steel tube, 65 inches of which were immersed in a sand bath heated to 410° C., at a flow rate of 1.5 mL/hr and a pressure of 20-25 psig. The flow rate of the solution was adjusted to give a residence time of the liquid feed in the heated zone of the tube of approximately 60 minutes. The effluent from the heated tube was collected in a pressurized vessel. After pumping the solution for a 26 hour period, no plugging or fouling of the tubing was observed.

EXAMPLE 4

42 mL of crude acetonitrile having the same composition as Example 1 was placed in the continuous reactor described in Example 3, and the reactor was heated to 72° C. 3.48 g of 25 weight percent aqueous NaOH solution and 2.11 g of 37 weight percent aqueous formaldehyde solution were added, and the mixture was stirred in the autoclave at 72°-80° C. for 1 hour. The reactor was then heated further until distillate began to collect in the receiver. Then feed pumps for crude acetonitrile, aqueous NaOH solution, aqueous formaldehyde solution, and bottoms removal were turned on, and the continuous distillation of treated crude solution was carried out for 80 minutes. During that time 104.0 mL of crude acetonitrile, 7.71 g of 25 weight percent aqueous NaOH solution, and 5.21 g of 37 weight percent aqueous formaldehyde solution were added, 72 mL of stabilized crude acetonitrile distillate were collected as a clear colorless liquid, and 21 mL of bottoms were recovered. Analysis of the stabilized crude acetonitrile distillate showed 69.1 weight percent acetonitrile, 24.3 weight percent $H_2O$, 0.07 weight percent acrylonitrile, 19 ppm HCN, and the remainder other organics.

The stabilized crude acetonitrile was mixed with a quantity of liquid ammonia such that the molar ratio of ammonia:acetonitrile was 0.25:1. The stabilized crude acetonitrile:ammonia solution was then pumped through a 1/16" type 316 stainless steel tube, 65 inches of which were immersed in a sand bath heated to 410° C., at a pressure of 20-25 psig. The flow rate of the solution was adjusted to give a residence time of the liquid feed in the heated zone of the tube of approximately 60 minutes. The effluent from the heated tube was collected in a pressurized vessel. After pumping the solution for a 33 hour period, 40.45 g of liquid was collected, and no plugging or fouling of the tubing was observed.

EXAMPLE 5

Approximately 150 mL of crude acetonitrile having the same composition as set forth in Example 1 was placed in a 1 L 3-neck flask affixed with thermometer, magnetic stir bar, reflux condenser, dropping funnel atop the reflux condenser, and distillation apparatus composed of a 30 cm vacuum jacketed fractionating column packed with glass helices and a coldfinger distillation head. The crude acetonitrile was heated with stirring to 79° C., and 3.6 mL of 50 weight percent aqueous NaOH solution were added dropwise over 10 minutes via the dropping funnel. The reflux condenser and dropping funnel were removed, and the reaction mixture was stirred at reflux (through the fractionating column) for 0.25 hours. Then the reflux condenser and dropping funnel are re-attached, and 7.2 mL of 37 weight percent aqueous formaldehyde solution containing 10-15 weight percent methanol were added dropwise over 5 minutes. The reflux condenser and dropping funnel were again removed, and the mixture was stirred at reflux for 30 minutes and then fractionally distilled. 79.9 g of distillate of boiling range 73.5°-81.5° C., stabilized crude acetonitrile, were collected. Analysis of the distillate showed 79.7 weight percent $CH_3CN$, 15.5 weight percent $H_2O$, 20.4 ppm HCN, and 4.8 weight percent acrylonitrile and other organics.

A 5 cc volume upward flow stainless steel microreactor (8 mm i.d.) was charged with 2 cc of a $BiMoFeO_x$ promoted catalyst, and the reactor was heated to 425° C. over 30 minutes in a molten salt bath with a flow of helium through the catalyst bed. After this time a flow of stabilized crude acetonitrile, oxygen, nitrogen, and gaseous ammonia was introduced over the catalyst. The stabilized crude acetonitrile was fed using a syringe metering pump, and the gaseous feeds were metered with mass flow controllers. The molar proportions of the feed were 1 $CH_3CN$:0.25 $NH_3$:1.7 $O_2$:6.3 $N_2$ with a contact time of 3 seconds. Reactants were fed for 43 minutes. The reactor effluent was collected in a scrubber containing 0.5N aqueous HCN. Analysis of the reactor effluent scrubber solutions showed production of HCN, CO, and $CO_2$, with HCN selectivity of 60.4% and $CH_3CN$ conversion of 43.9%.

EXAMPLE 6

A 5 cc volume upward flow stainless steel microreactor (8 mm i.d.) was charged with 2 cc of a $BiMoFeO_x$ promoted catalyst, and the reactor was heated to 425° C. over 30 minutes in a molten salt bath with a flow of helium through the catalyst bed. After this time, a flow of stabilized crude acetonitrile prepared as in Example 5, oxygen, and nitrogen was introduced over the catalyst. The stabilized crude acetonitrile was fed using a syringe metering pump, and the gaseous feeds were metered with mass flow controllers. The molar proportions of the feed were 1 $CH_3CN$:1.7 $O_2$:6.3 $N_2$ with a contact time of 3 seconds. Reactants were fed for 52 minutes. The reactor effluent was collected in a scrubber containing 0.5N aqueous HCl. Analysis of the reactor effluent scrubber solutions showed production of HCN, CO, and $CO_2$, with HCN selectivity of 22.4% and $CH_3CN$ conversion of 54%.

The foregoing description of the preferred embodiments of the invention have been presented for purpose of illustration and description. They are not intended to be exhaustive or to limit the invention to the precise form disclosed and obviously many modifications and variations are possible in light of the above teaching. The embodiments were chosen and described in order to best explain the principles of the invention and its practical application. It is intended that the scope of the invention be defined by the claims appended hereto.

What we claim is:

1. A process for stabilizing crude acetonitrile comprising:
   (a) mixing crude acetonitrile with a strong base and aldehyde to form a mixture, wherein said mixture has a pH greater than 10,
   (b) heating said mixture to its reflux temperature for a time sufficient to enable said crude acetonitrile to stabilize, and
   (c) recovering said stabilized crude acetonitrile from said mixture.
2. The process of claim 1 wherein the base is an alkali hydroxide.
3. The process of claim 2 wherein the aldehyde is formaldehyde.
4. The process of claim 2 wherein the mixture of step (a) has a pH between about 10 to 14.
5. The process of claim 3 wherein the mixture of step (a) has a pH between about 11 to 14.
6. The process of claim 5 wherein the pH is between about 12 to 13.8.

* * * * *